US00PP28621P2

(12) United States Plant Patent
Hansen

(10) Patent No.: US PP28,621 P2
(45) Date of Patent: Nov. 7, 2017

(54) ***SEDUM* PLANT NAMED 'WILDFIRE'**

(50) Latin Name: ***Sedum* hybrid**
Varietal Denomination: Wildfire

(71) Applicant: Christopher M. Hansen, Zeeland, MI (US)

(72) Inventor: Christopher M. Hansen, Zeeland, MI (US)

( * ) Notice: Subject to any disclaimer, the term of this patent is extended or adjusted under 35 U.S.C. 154(b) by 86 days.

(21) Appl. No.: 14/998,569

(22) Filed: Jan. 19, 2016

(51) Int. Cl.
*A01H 5/02* (2006.01)

(52) U.S. Cl.
USPC ..... Plt./479

(58) Field of Classification Search
USPC ..... Plt./263.1, 479
See application file for complete search history.

*Primary Examiner* — Susan McCormick Ewoldt
*Assistant Examiner* — Karen Redden
(74) *Attorney, Agent, or Firm* — Penny J. Aguirre

(57) ABSTRACT

A new cultivar of *Sedum* plant named 'Wildfire' characterized by its variegated foliage that emerges with a tri-color look of green, pink and yellow in the spring and turns bright shiny cherry red in color with bright orange-pink margins as it matures in full sun with color retention throughout the entire growing season, its heavy branching with branches from every leaf node along the stems producing a mounded groundcover-type plant habit with no open centers and that does not flop in the summer, and its large inflorescences that are pink in color and appear in late summer.

2 Drawing Sheets

Botanical classification: *Sedum* hybrid.
Variety denomination: 'Wildfire'.

BACKGROUND OF THE INVENTION

The present invention relates to a new and distinct cultivar of *Sedum* plant, botanically of hybrid origin and known as *Sedum* 'Wildfire' and referred to hereinafter by its cultivar name, 'Wildfire'. The new cultivar of *Sedum* is a hardy herbaceous perennial grown for use as a landscape and container plant and is particularly suitable as a groundcover.

The Inventor discovered the new cultivar in November of 2013 as a naturally occurring branch mutation of *Sedum* 'Firecracker' (U.S. Plant Pat. No. 26,595) that was growing in a 72-cell plug tray at his nursery in Hudsonville, Mich.

Asexual propagation of the new cultivar was first accomplished by stem tip cuttings in March of 2014 in Hudsonville, Mich. Asexual propagation by stem tip cuttings has determined the characteristics to be stable and reproduced true to type in successive generations.

SUMMARY OF THE INVENTION

The following traits have been repeatedly observed and are determined to be the characteristics of the new cultivar. These attributes in combination distinguish 'Wildfire' as a unique cultivar of *Sedum*.

1. 'Wildfire' exhibits variegated foliage that emerges with a tri-color look of green, pink and yellow in the spring and turns bright shiny cherry red in color with bright orange-pink margins as it matures in full sun (yellow edges when grown in shade) with color retention without fading throughout the entire growing season.
2. 'Wildfire' exhibits heavy branching with branches from every leaf node along the stems producing a mounded groundcover-type plant habit with no open centers and that does not flop in the summer.

3. 'Wildfire' exhibits a very vigorous vegetative bud production when entering winter dormancy in early November with at least 50 new growth buds in a 30-cell plug.
4. 'Wildfire' exhibits large inflorescences that are pink in color and appear in late summer.

The parent of 'Wildfire', 'Firecracker', is similar to 'Wildfire' in having similar inflorescences and in plant habit. 'Firecracker' differs from 'Wildfire' in having leaves with no variegation that are solid red in color. 'Wildfire' can be most closely compared to the *Sedum* cultivar 'Lime Twister' (U.S. Plant Pat. No. 26,895) and the *Sedum spurium* cultivar 'Tricolor' (not patented). Both cultivars are similar to 'Wildfire' in having variegated foliage and in having a mounded groundcover-type plant habit. 'Lime Twister' differs from 'Wildfire' in having foliage that is green in color with margins that are creamy yellow-white in color, in having a plant size that is 20% smaller, in having leaves that are 30% smaller in size and in having flowers that are lighter pink in color. 'Tricolor' differs from 'Wildfire' in having leaves that is blue-green in color with margins that are creamy white-pink in color, 75% smaller in size and thinner in substance, in having a plant height that is 40% smaller, and in having inflorescences that are smaller in size, lighter pink in color and an earlier blooming period.

BRIEF DESCRIPTION OF THE DRAWINGS

The accompanying colored photographs illustrate the overall appearance and distinct characteristics of the new *Sedum*. The photographs were taken of a plant about 5 months in age (from a 30-cell plug) as grown outdoors in a 1-gallon container in Hudsonville, Mich.

The photograph in FIG. 1 provides a view of the foliage of 'Wildfire' in spring.

Figure 1:
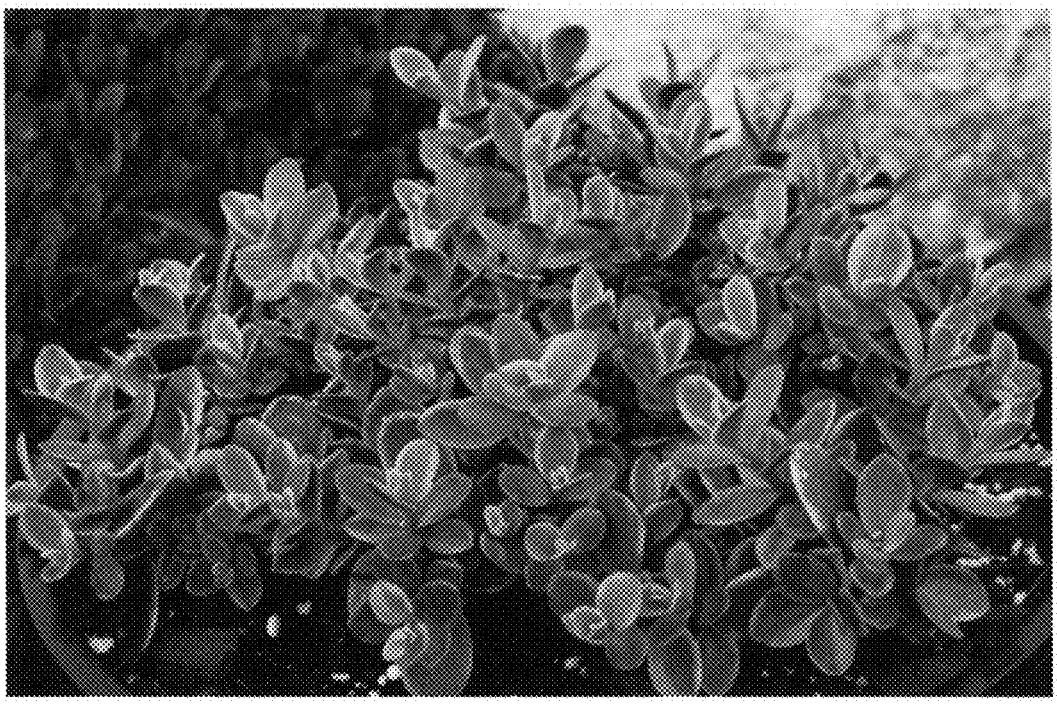
Figure 2:
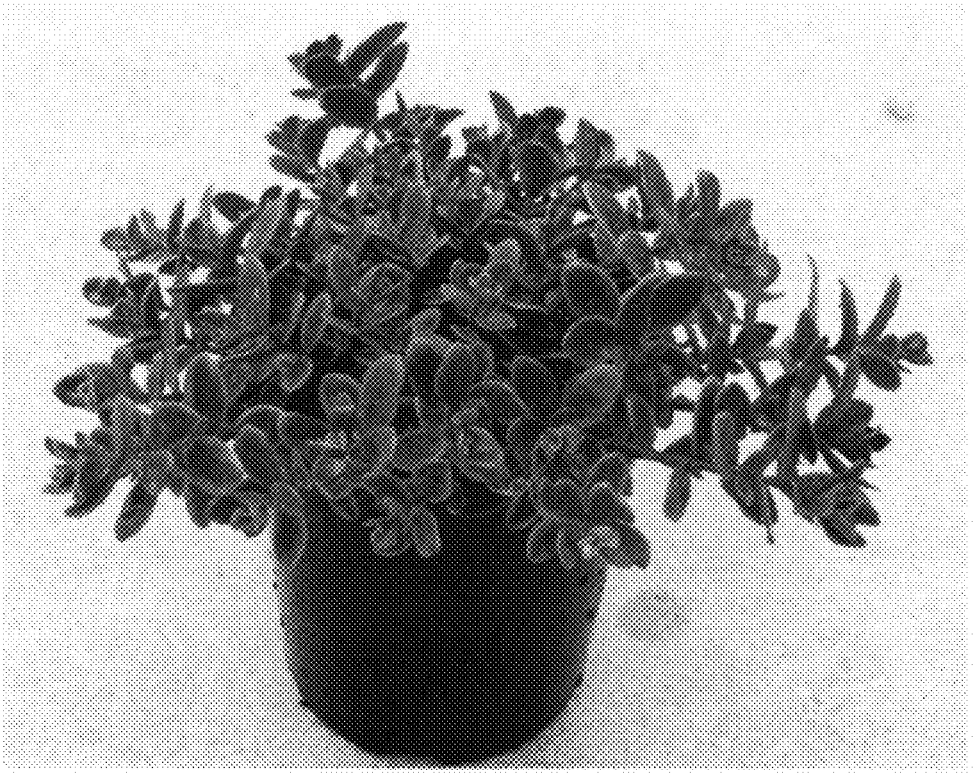

The photograph in FIG. 2 provides a view of the plant habit and foliage coloration of 'Wildfire' in summer through fall when grown in full sun.

Figure 3:
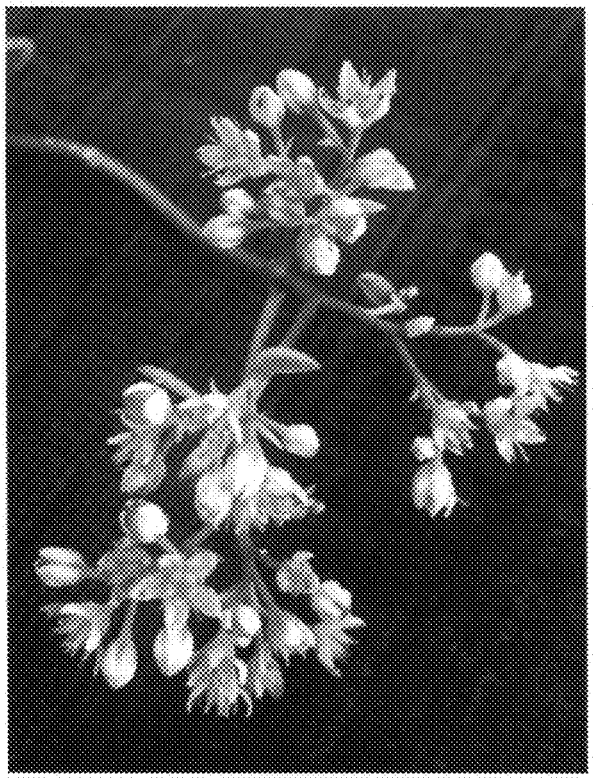

The photograph in FIG. 3 provides a close-up view of the inflorescences of 'Wildfire'.

The colors in the photographs may differ slightly from the color values cited in the detailed botanical description, which accurately describe the colors of the new *Sedum*.

DETAILED BOTANICAL DESCRIPTION

The following is a detailed description of the new cultivar as observed on 3 month-old plants of 'Wildfire' as grown outdoors in two-quart containers in Hudsonville, Mich. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—5 weeks in mid to late summer in Hudsonville, Mich.

*Plant type.*—Herbaceous perennial.

*Plant habit.*—Spreading mound, ground-cover, well-branched.

*Height and spread.*—Reaches an average of 15.3 cm in height and about 45.7 cm in spread as grown outdoors in a one-gallon container.

*Hardiness.*—At least hardy in U.S.D.A. Zones 4 to 9.

*Diseases pest.*—High resistance to *Sedum* foliage blight caused by *Colletotrichum* spp.), no occurrences have been observed in the last 4 years of observation.

*Root description.*—Fibrous, 199D in color.

*Propagation.*—Stem cuttings and division.

*Growth rate.*—Vigorous.

*Root development.*—An average of ten days for root initiation and about eight weeks to produce a young rooted plant in a 72-cell plug.

*Drought tolerance.*—Highly drought tolerant.

Stem description:

*Stem shape.*—Oval.

*Stem size.*—Basal and secondary branches; an average of 8 cm in length and 2.5 mm in width.

*Internode length.*—Average of 8 mm with terminal leaves whorled (<0.5 mm).

*Stem color.*—182A on new growth, 178A on mature growth.

*Stem surface.*—Glabrous.

*Branching habit.*—Numerous basal branches (about 20 in a 2-qt container) and at least 50 new growth buds are observed in a 30-cell plug when entering winter dormancy.

Foliage description:

*Leaf shape.*—Elliptic.

*Leaf division.*—Simple.

*Leaf arrangement.*—Opposite (sometimes whorled).

*Leaf base.*—Cuneate.

*Leaf apex.*—Broadly acute-rounded.

*Leaf venation.*—Not conspicuous, color matched leaf color.

*Leaf margins.*—Entire to very slightly undulated.

*Leaf attachment.*—Sessile.

*Leaf orientation.*—Primarily horizontal and held flat.

*Leaf substance.*—Thick, succulent.

*Leaf surface texture.*—Glandular and very slightly glaucous.

*Leaf color.*—Spring upper and lower surface; a blend of 147A with margins 158A to 158B, mid-summer and fall upper and lower surface, N187A and slightly suffused with 147A with margins 182A.

*Leaf size.*—Average of 2.8 cm in length and 1.7 cm in width when mature.

Flower description:

*Inflorescence type.*—Dense, slightly rounded cymes with an average of 4 terminal forked branches at terminus and upper lateral nodes.

*Inflorescence size.*—An average of 3.3 cm in depth and 5.5 cm in width.

*Lastingness of inflorescence.*—At least one month.

*Flower type.*—Perfect, 5-starred.

*Flower number.*—An average of 65 flowers per branched cyme.

*Flower fragrance.*—None.

*Flower buds.*—Conical in shape, an average of 4.2 mm length and 2.3 mm in diameter, ribbed surface, color; 155C suffused with N74B to N74D.

*Flower size.*—An average of 3 cm in depth and 5 mm in diameter.

*Peduncles.*—Round in shape, up to 2 cm in length, an average of 1 mm in width, secondary peduncle; 7 mm in length and 0.7 mm in width, both strong and flexible in strength with glabrous and shiny surfaces, color; 139B heavily suffused with 178A, peduncle leaves; fleshy, an average of 2 per individual cyme, elliptic in shape, entire margins, acute apex, cuneate base, an average of 5.5 mm in length and 2 mm in width, color; 138A heavily suffused with 61A especially at the apex, smooth, shiny, and minutely scaberulose upper and lower surfaces.

*Pedicels.*—Round in shape, an average of 4 mm in length and 0.5 mm in width, color; N138B and lightly suffused with 61A, strong and flexible in strength, glabrous and minutely scaberulose surface, pedicel leaves; irregularly distributed 1 per pedicel when present; an average of 1 mm in length and 0.5 mm in width, elliptic in shape, entire margins, acute apex, cuneate base, color; 138A very heavily suffused with 61A especially at the apex, smooth, shiny, and minutely scaberulose upper and lower surfaces.

*Sepals.*—5, lanceolate in shape, entire margin, acute apex, truncate base, an average of 2 mm in length and 0.8 mm in width, color of inner and outer surfaces; N138B to N138C suffused with 61A, glabrous and smooth on both surfaces.

*Petals.*—5, rotate to upright, elliptic to oval in shape, truncate base, acute apex, entire margin, about 3 mm in length and 1.5 mm in width, color of inner and outer surfaces when opening; a blend between N155B and 70D, color of inner and outer surfaces when mature; 75B, glabrous and shiny on both surfaces.

Reproductive organs:

*Pistils*.—5, showy, held erect, about 2 mm in length, stigma; minute, about 0.2 mm in length and 83A in color, style; lanceolate in shape, an average of 1.8 mm in length and 0.5 mm in width, a blend of 70A to 70D in color, ovary; small, single celled and translucent in color.

*Stamens*.—10, an average of 3 mm in length, filament; very fine and a mix of 70A to 70D in color, basifixed anther; about 0.5 mm in length and width and 187A in color, pollen is low in quantity and too minimal for color determination.

*Fruit and seed*.—Has not ben observed to date.

It is claimed:

1. A new and distinct variety of *Sedum* plant named 'Wildfire' as described and illustrated herein.

* * * * *